US010448806B2

(12) United States Patent
Wright et al.

(10) Patent No.: US 10,448,806 B2
(45) Date of Patent: Oct. 22, 2019

(54) ENDOSCOPE DESIGNS AND METHODS OF MANUFACTURE

(71) Applicant: Integrated Endoscopy, Inc., Rancho Santa Margarita, CA (US)

(72) Inventors: George Wright, Dove Canyon, CA (US); Kais Almarzouk, Tustin, CA (US); Lonnie R. Hoyle, Mission Viejo, CA (US)

(73) Assignee: Integrated Endoscopy, Inc., Irvine, CA (US)

( * ) Notice: Subject to any disclaimer, the term of this patent is extended or adjusted under 35 U.S.C. 154(b) by 0 days.

(21) Appl. No.: 13/786,220

(22) Filed: Mar. 5, 2013

(65) Prior Publication Data

US 2013/0345507 A1 Dec. 26, 2013

Related U.S. Application Data

(63) Continuation of application No. 13/176,681, filed on Jul. 5, 2011, which is a continuation of application
(Continued)

(51) Int. Cl.
*A61B 1/00* (2006.01)
*A61B 1/055* (2006.01)
(Continued)

(52) U.S. Cl.
CPC .......... *A61B 1/00096* (2013.01); *A61B 1/042* (2013.01); *A61B 1/055* (2013.01);
(Continued)

(58) Field of Classification Search
CPC . A61B 1/0684; A61B 1/00101; A61B 1/0676; A61B 1/00177; A61B 1/00181; A61B 1/0623
(Continued)

(56) References Cited

U.S. PATENT DOCUMENTS 1,632,290 A * 6/1927 Heymer ........................ 600/171
4,148,550 A 4/1979 Macanally
(Continued)

FOREIGN PATENT DOCUMENTS

JP 11-47080 2/1999
JP 2002-148520 5/2002
(Continued)

OTHER PUBLICATIONS

Notice of Reasons for Rejection dated Jun. 18, 2013 in corresponding Japanese Pat. App. No. 2011-151631 in five (5) pages.
(Continued)

*Primary Examiner* — Alexandra L Newton
(74) *Attorney, Agent, or Firm* — Knobbe, Martens, Olson & Bear LLP (57) ABSTRACT

Various embodiments of the present invention comprise endoscopes for viewing inside a cavity of a body such as a vessel like a vein or artery. These endoscopes may include at least one solid state emitter such as a light emitting diode (LED) that is inserted into the body cavity to provide illumination therein. Certain embodiments of the invention comprise disposable endoscopes that can be fabricated relatively inexpensively such that discarding these endoscopes after a single use is cost-effective. The endoscope may comprise a lens holder on a distal end of the endoscope for collection of light reflected from surfaces within the body in which the endoscope is inserted. This lens holder may have an inner cavity through which light passes along an optical path. Reflective surfaces on sidewalls of the inner cavity may direct light along this optical path. The endoscope may further comprise an elongated support structure for supporting a plurality of lenses disposed along the optical path. This optical path may lead to a detector onto which images are formed.

25 Claims, 5 Drawing Sheets

Related U.S. Application Data

No. 11/099,435, filed on Apr. 5, 2005, now Pat. No. 7,976,462.

(60) Provisional application No. 60/559,813, filed on Apr. 6, 2004.

(51) Int. Cl.
| | | |
|---|---|---|
| *A61B 1/06* | (2006.01) | |
| *A61B 1/313* | (2006.01) | |
| *A61B 1/04* | (2006.01) | |
| *A61B 1/07* | (2006.01) | |

(52) U.S. Cl.
CPC .......... *A61B 1/0676* (2013.01); *A61B 1/0684* (2013.01); *A61B 1/07* (2013.01); *A61B 1/3137* (2013.01); *A61B 1/00179* (2013.01)

(58) Field of Classification Search
USPC .............................. 600/170, 171, 175, 176
See application file for complete search history.

(56) References Cited

U.S. PATENT DOCUMENTS

| | | | | |
|---|---|---|---|---|
| 4,730,909 | A | * | 3/1988 | Takahashi .......... G02B 23/2423 359/735 |
| 4,784,118 | A | | 11/1988 | Fantone |
| 4,850,342 | A | | 7/1989 | Hashiguchi et al. |
| 5,020,893 | A | | 6/1991 | Karst et al. |
| 5,142,410 | A | | 8/1992 | Ono et al. |
| 5,601,525 | A | | 2/1997 | Okada |
| 5,647,840 | A | | 7/1997 | D'Amelio et al. |
| 5,666,222 | A | | 9/1997 | Ning |
| 5,700,236 | A | * | 12/1997 | Sauer et al. .................. 600/175 |
| 5,865,725 | A | | 2/1999 | Arai et al. |
| 5,980,453 | A | | 11/1999 | Forkey et al. |
| 5,999,344 | A | | 12/1999 | Wulfsberg et al. |
| 6,248,060 | B1 | | 6/2001 | Buess et al. |
| 6,364,830 | B1 | | 4/2002 | Durell |
| 6,398,723 | B1 | | 6/2002 | Kehr et al. |
| 6,424,473 | B1 | | 7/2002 | Nakane et al. |
| 6,471,640 | B1 | | 10/2002 | Holger |
| 6,635,010 | B1 | | 10/2003 | Lederer |
| 6,638,216 | B1 | * | 10/2003 | Durell ........................... 600/173 |
| 6,692,431 | B2 | | 2/2004 | Kazakevich |
| 6,701,181 | B2 | | 3/2004 | Tang et al. |
| 6,818,818 | B2 | | 11/2004 | Bareis |
| 6,855,109 | B2 | | 2/2005 | Obata et al. |
| 6,921,920 | B2 | | 7/2005 | Kazakevich |
| 6,962,565 | B2 | | 11/2005 | Nakamura |
| 7,063,663 | B2 | | 6/2006 | Kazakevich |
| 7,345,312 | B2 | | 3/2008 | Kazakevich |
| 7,413,543 | B2 | | 8/2008 | Banik et al. |
| 7,540,645 | B2 | | 6/2009 | Kazakevich |
| 7,683,926 | B2 | | 3/2010 | Schechterman et al. |
| 7,896,804 | B2 | | 3/2011 | Uchimura |
| 7,959,338 | B2 | | 6/2011 | Kazakevich |
| 7,976,462 | B2 | | 7/2011 | Wright |
| 8,636,652 | B2 | | 1/2014 | Wright |
| 8,959,338 | B2 | | 2/2015 | Snow et al. |
| 2002/0103420 | A1 | | 8/2002 | Coleman et al. |
| 2002/0154215 | A1 | | 10/2002 | Schechterman et al. |
| 2002/0183623 | A1 | | 12/2002 | Tang et al. |
| 2003/0018238 | A1 | | 1/2003 | Obata et al. |
| 2003/0042493 | A1 | | 3/2003 | Kazakevich |
| 2003/0050534 | A1 | * | 3/2003 | Kazakevich .......... A61B 1/0607 600/178 |
| 2003/0120129 | A1 | | 6/2003 | Nakamura |
| 2004/0031517 | A1 | | 2/2004 | Bareis |
| 2004/0092794 | A1 | * | 5/2004 | Chin et al. .................... 600/146 |
| 2005/0075538 | A1 | | 4/2005 | Banik et al. |
| 2006/0041193 | A1 | | 2/2006 | Wright et al. |
| 2006/0258902 | A1 | | 11/2006 | Spivey et al. |
| 2006/0293565 | A1 | | 12/2006 | Uchimura |
| 2007/0173695 | A1 | | 7/2007 | Hirata |
| 2008/0062540 | A1 | | 3/2008 | Scholer |
| 2008/0130311 | A1 | | 6/2008 | Kazakevich |
| 2009/0018397 | A1 | | 1/2009 | Scholly et al. |
| 2009/0219713 | A1 | | 9/2009 | Siemiet et al. |
| 2011/0092772 | A1 | | 4/2011 | Weber et al. |
| 2011/0263941 | A1 | | 10/2011 | Wright et al. |
| 2012/0029289 | A1 | | 2/2012 | Kucklick |
| 2012/0176669 | A1 | | 7/2012 | Kiedrowski |
| 2013/0345507 | A1 | | 12/2013 | Wright et al. |
| 2015/0164312 | A1 | | 6/2015 | Hoyle et al. |

FOREIGN PATENT DOCUMENTS

| | | |
|---|---|---|
| JP | 2002-148520 A | 5/2002 |
| JP | 2002-224015 | 8/2002 |
| JP | 2003-021792 | 1/2003 |
| JP | 2003-024276 | 1/2003 |
| WO | WO 98/35607 | 8/1998 |
| WO | WO 98/35607 A1 | 8/1998 |
| WO | WO 03/022135 | 3/2003 |
| WO | WO 03/022135 A2 | 3/2003 |
| WO | WO 03/022435 | 3/2003 |
| WO | WO 2004/036266 | 4/2004 |

OTHER PUBLICATIONS

U.S. Appl. No. 12/974,452, filed Dec. 21, 2010, Methods and Systems for Disabling an Endoscope After Use.
U.S. Appl. No. 12/975,060, filed Dec. 21, 2010, Scope With Different Color Light Sources.
U.S. Appl. No. 12/975,062, filed Dec. 21, 2010, Systems and Methods for Endoscopic Imaging With Monochromatic Detector.
U.S. Appl. No. 14/567,879, filed Dec. 11, 2014, Medical Imaging Device Using Thermall Conducting Lens Cradle.
International Search Report and Written Opinion for International Application No. PCT/US2005/11279, dated Jun. 27, 2007.
Supplemental European Search Report issued in European Application No. 05732799.1 dated Aug. 10, 2009.
Office Action dated Jun. 16, 2010, issued by European Patent Office for European Patent Application No. 05 732 799.1.
Japan Patent Office; Office Action; Patent Application No. 2007-507398 (dated Jan. 5. 2011).
Office Action dated Dec. 10, 2009 issued in U.S. Appl. No. 11/099,435.
Office Action dated Jul. 9, 2010 issued in U.S. Appl. No. 11/099,435.
Notice of Reasons for Rejection mailed by the Japan Patent Office dated Jan. 10, 2012 in corresponding Japanese Patent App. No. 2007-507398 in 6 pages.
International Search Report and Written Opinion dated Apr. 13, 2015 in International Application No. PCT/US2014/069842.
Restriction Requirement issued in U.S. Appl. No. 14/567,879 dated Jan. 31, 2017, in 9 pages.
Response to Restriction Requirement filed in U.S. Appl. No. 14/567,879 dated May 1, 2017, in 7 pages.
Non-Final Office Action in U.S. Appl. No. 14/567,879 dated Jun. 1, 2017, in 17 pages.
Response to Non-Final Office Action in U.S. Appl. No. 14/567,879 dated Nov. 30, 2017, in 14 pages.
Final Office Action in U.S. Appl. No. 14/567,879 dated Mar. 8, 2018, in 23 pages.
Response to Final Office Action in U.S. Appl. No. 14/567,879 dated Sep. 7, 2018, in 10 pages.
Notice of Allowance in U.S. Appl. No. 14/567,879 dated Mar. 20, 2019, in 13 pages.

* cited by examiner

ENDOSCOPE DESIGNS AND METHODS OF MANUFACTURE

RELATED APPLICATIONS

This application is a continuation of U.S. application Ser. No. 13/176,681, filed Jul. 5, 2011, which is a continuation of U.S. application Ser. No. 11/099,435, filed Apr. 5, 2005, now U.S. Pat. No. 7,976,462, which claims the benefit of U.S. Provisional Application No. 60/559,813, filed Apr. 6, 2004, all of which are incorporated by reference herein.

BACKGROUND

Field of the Invention

The present invention relates generally to optical systems, and in some embodiments, to endoscopes and other medical devices.

Description of the Related Art

Endoscopes generally include a tube with imaging optics to be inserted into a patient. Illumination may be provided by a source that is located external to the patient. Light from the illumination source may travel via a conduit, such as a fiberoptic or fiberoptic bundle, through the tube into the patient. The light may be emitted inside of the patient at the tube's distal end near a treatment or viewing site. Features inside the body are likewise illuminated and can be viewed using the imaging optics, which form images of the patient's insides.

SUMMARY

In one embodiment, an endoscope has proximal and distal end portions for viewing inside a cavity of a body. The endoscope comprises: one or more solid state emitters having an electrical input and an optical output, said one or more solid state emitters disposed at said distal end portion of said endoscope, said one or more solid state emitters radiating light when activated so as to illuminate at least a portion of said cavity in said body; an optical path extending from said distal end portion to said proximal end portion for propagating light from said distal end portion to said proximal end portion of said endoscope such that an image of an object at said distal end portion can be formed at said proximal end portion; and an electrically conducting path from said proximal end portion to said distal end portion of said endoscope, said electrically conducting path electrically connected to said electrical input of said one or more solid state emitters for providing electrical power to said one or more solid state emitters.

In another embodiment, an endoscope has proximal and distal end portions for viewing features inside a body into which said distal end portion of said endoscope is inserted. The endoscope comprises: a longitudinal member extending from said distal end portion to said proximal end portion, said longitudinal member having an inner cavity region; an optical path through said inner cavity region of said longitudinal member for propagating light from said distal end portion to said proximal end portion of said endoscope; and a first specularly reflective metalized non-glass surface disposed along said optical path at said distal end portion of said longitudinal member, said first specularly reflective metalized surface angled such that light can be collected at said distal end portion from an oblique direction with respect of said longitudinal member.

In yet another embodiment, a battery operated hand-held endoscope instrument has proximal and distal end portions for producing images of internal regions of a body. The endoscope instrument comprises: one or more solid state emitters having an electrical input and an optical output, said one or more solid state emitters disposed at said distal end portion of said endoscope instrument, said one or more solid state emitters for illuminating said internal regions of said body; an optical path extending from said distal end portion to said proximal end portion for propagating light from said distal end portion to said proximal end portion of said endoscope instrument to form an image at said proximal end portion; an electrically conducting path from said proximal end portion to said distal end portion of said endoscope, said electrically conducting path electrically connected to said electrical input of said one or more solid state emitters for providing electrical power from a battery at said proximal end portion to said one or more solid state emitters at said distal end portion; an optical sensor disposed at said proximal end portion of said endoscope, said optical sensor comprising an optical sensor having an electrical power input and electrical signal output; and a wireless transmitter electrically connected to said electrical signal output of said optical sensor so as to receive electrical signals from said electrical signal output of said optical sensor corresponding to images formed on said optical sensor.

In one embodiment, a endoscope has proximal and distal ends for viewing features inside a body. The endoscope comprises: a plurality of rod lenses aligned along an optical path; a slotted elongate support structure comprising a plurality of slots in which said plurality of rod lenses respectively fit so as to be aligned along said optical path; and an outer tube with a hollow inner region, said elongated support structure together with said plurality of rod lens disposed in said hollow inner region of said out tube, wherein said slots are separated with respect to each other so as to establish suitable spacing between said lenses to relay an image of a feature in said body to said proximal end portion.

In another embodiment, a method of manufacturing an endoscope assembly for viewing portions of a body, said endoscope assembly having a distal end portion and a proximal end portion, comprises: providing an elongated support structure having a plurality of sites for insertion of optical elements; inserting a plurality of lenses at said sites; inserting said elongated support structure into a hollow outer protective shield having an open inner region, wherein said plurality of sites are laterally positioned and longitudinally spaced from with respect to each other so as to provide an aligned optical system that relays an image from said distal end portion to said proximal end portion.

In another embodiment, a method of manufacturing a front end of an endoscope for viewing portions of a body comprises: forming a front endpiece, said front endpiece for receiving light from said body portions to enable viewing of said body portions; forming an inner cavity region in said front endpiece, said inner cavity region for passage of said light from said body portions; forming at least one substantially planar sidewall surface in said inner cavity region; and metalizing said at least one substantially planar sidewall surface so as to form a substantially reflective surface that reflects said light received from said body portions.

In yet another embodiment, a head for an endoscope for viewing objects comprises: a main body having a front and a rear, said front to be disposed with respect to said object such that light from said object propagates toward said front of said main body; an inner open region in said main body, light from said object propagating into said inner open region, said inner open region defined by interior sidewalls of said main body; and apertures at said front and rear of said main body providing access to said inner open region, wherein at least one of said sidewalls is coated with a substantially reflective material and is substantially smooth so as to form a substantially reflective surface, said reflective surface reflecting light from said object such that an image of said object can be formed.

In one embodiment, a disposable endoscope for viewing features inside a body comprises: a longitudinal member having distal and proximal ends and an inner cavity region therein, said longitudinal member further comprising an end portion at said distal end with an aperture therein for entry of light into said inner cavity, at least said end portion comprising plastic; one or more solid state emitters disposed at said distal end of said longitudinal member for providing illumination; and an optical path through said inner cavity region of said longitudinal member for propagating light from said distal end to said proximal end of said longitudinal member, said optical path including at least one optical element, wherein said end portion of said longitudinal member includes reflective material formed on said plastic in said end portion of said longitudinal member to reflect light received through said aperture along said optical path to said proximal end portion of said longitudinal member.

In another embodiment, a disposable endoscope for viewing features inside a body comprises: a longitudinal member having distal and proximal ends and an inner cavity region therein, said longitudinal member further comprising an end portion at said distal end with an aperture therein for entry of light into said inner cavity, at least said end portion comprising ceramic material; one or more solid state emitters disposed at said distal end of said longitudinal member for providing illumination; and an optical path through said inner cavity region of said longitudinal member for propagating light from said distal end to said proximal end of said longitudinal member, said optical path including at least one optical element, wherein said end portion of said longitudinal member includes reflective material formed on said ceramic material in said end portion of said longitudinal member to reflect light received through said aperture along said optical path to said proximal end portion of said longitudinal member.

DETAILED DESCRIPTION OF PREFERRED EMBODIMENTS

Embodiments of the present invention comprise endoscopes for viewing inside a cavity of a body such as a vessel like a vein or artery or elsewhere. The endoscopes have a light source that is configured, sized and positioned so as to be inserted into the body cavity to provide illumination therein. In various embodiments, this light source comprises at least one solid state emitter such as a light emitting diode (LED). Preferably, this solid state emitter is small and bright. Light emitted from the light source is reflected off objects or walls in the interior of the body cavity. A portion of the reflected light is collected through an aperture in the endoscope. This light is directed along an optical path through the endoscope so as to form an image of the objects or walls. In certain embodiments, the optical path includes a series of lenses such as rod lenses disposed in a support structure or cradle. The light is then directed to an optical sensor such as, for example, an optical detector array or an optical camera. Thus, an image of the object inside the body cavity can be viewed.

Figure 1:
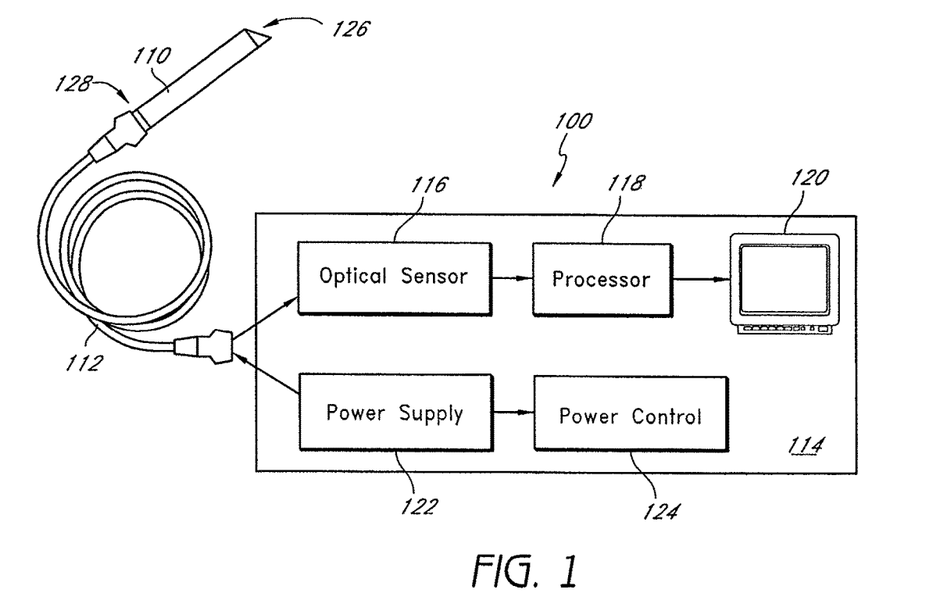
FIG. 1 illustrates one system for producing images of features inside of body parts.

FIG. 1 illustrates one system 100 according to an embodiment of the invention for producing images such as electronic, e.g., video or digital, images of features inside, for example, body parts. The system 100 includes an endoscope structure 110 coupled to an imaging and control apparatus 114 through a cable 112. The imaging and control apparatus 114 includes an optical sensor 116, a processor 118, a display 120, a power supply 122, and a power control 124.

The endoscope structure 110 comprises an elongated member that is inserted into a portion of a body such as a human body. This endoscope structure 110 includes a distal end portion 126 and a proximal end portion 128. One or more solid state emitters (not shown) are preferably disposed at the distal end portion 126. The solid state emitters each include an electrical input and have an optical output. The solid state emitters may comprise, for example, light emitting diodes (LEDs). Preferably, these solid state emitters are bright and small. In some embodiments, for example, these solid state emitters radiate over 10 lumens. These LED may be less than a millimeter and in some embodiments may be about 0.5 millimeters. The large brightness and small size of these emitters enables such endoscopes to have a smaller cross-section than conventional endoscopes that rely on large optical fiber bundles to provide illumination. Reduced size offers the advantage that the endoscope is less intrusive and causes less damage and trauma to the body. A plurality of such small solid state emitters may be disposed at the distal end of the endoscope structure 110. In certain embodiments 2, 3, 4, 5, 6, 7, 8, or more emitters are employed. In some embodiments, these emitters emit white light although emitters need not be white light emitters. Colored emitters and emitters that radiate in narrow wavelength ranges may be employed as well. For example, images may be formed by optical sensors 116 that are sensitive to the particular wavelength region used for illumination. In certain embodiments, a specific wavelength illumination may be employed for fluorescence applications.

The solid state emitters radiate light and illuminate a portion of a body cavity. Accordingly, the distal end 126 of the endoscope structure 110 includes an aperture (not shown) for collecting light reflected or scattered from the illuminated portion of the body cavity. The light collected through the aperture is transferred along an optical path (not shown) from the distal end 126 of the endoscope structure 110 to the proximal end 128. Preferably, features in the illuminated portion of the cavity are imaged and the image is relayed along the optical path so as to form an image of a portion of the body cavity at the proximal end 128.

Accordingly, the light and image are transferred from the proximal end 128 of the endoscope structure 110 through the cable 112 to the imaging and control apparatus 114. Accordingly, the cable preferably comprises a system of relay lens or a coherent fiber bundle. The cable preferably transfers the image to the optical sensor 116 in the imaging apparatus 114. The optical sensor 116, which may comprise a detector array such as a CCD or CMOS sensor array, has a light sensitive optical input that receives the light from the cable 112. The optical sensor 116 preferably further comprises an electrical signal output for outputting an electrical signal corresponding to the image of the illuminated portion of the body cavity. The electrical signal from the optical sensor 116 is transmitted to a processor 118 and onto a on the display device 120 such as a video screen or computer monitor. Although not shown, alternative embodiments may include transmitting the electrical signal from the optical sensor 116 directly to the display device 120, for example, when the optical sensor 116 performs the processing.

As discussed above, in certain embodiments the cable 112 comprises a fiber optic such as a coherent fiber optic bundle. The cable 112 also preferably includes electrical power lines (not shown), such as thin electrical leads or wires, that provide electrical power to the solid state emitters disposed at the distal end 126 of the endoscope 110. The electrical power lines are electrically coupled to the power supply 122. This power supply 122 may, for example, provide 12 or 24 volts and 20 milliamps to 1.5 Amp of current, however, voltages and currents outside these ranges are possible. The power supply 122 may be controlled by the power controller 124. The power controller 124 may, for example, enable the current supplied to the solid state emitters at the distal end 126 of the endoscope structure 110 to be adjusted. Accordingly, the brightness or intensity of the light emitted from the solid state emitters can be adjusted. In one embodiment, the power control comprises a rheostat.

Although the cable 112 is included in the endoscope system 100 shown in FIG. 1, this cable is not required. In other embodiment, this cable 112 may be excluded. For example, the optical sensor 116 may be disposed at the proximal end portion 128 of the endoscope structure 110. In such designs, electrical cable may be connected to the endoscope structure 110 to power the one or more solid state emitters at the distal end portion 126.

In certain embodiments, the endoscope structure 110 is disposable. Various design features discussed more fully below may reduce the cost of the endoscope structures 110 such that the endoscope structure need not be reused over and over but may be discarded after use. In some embodiments, the endoscope structure 110 may plug into the cable 112 and thus may be detached and disposed of and replaced for the next procedure.

Figure 2:
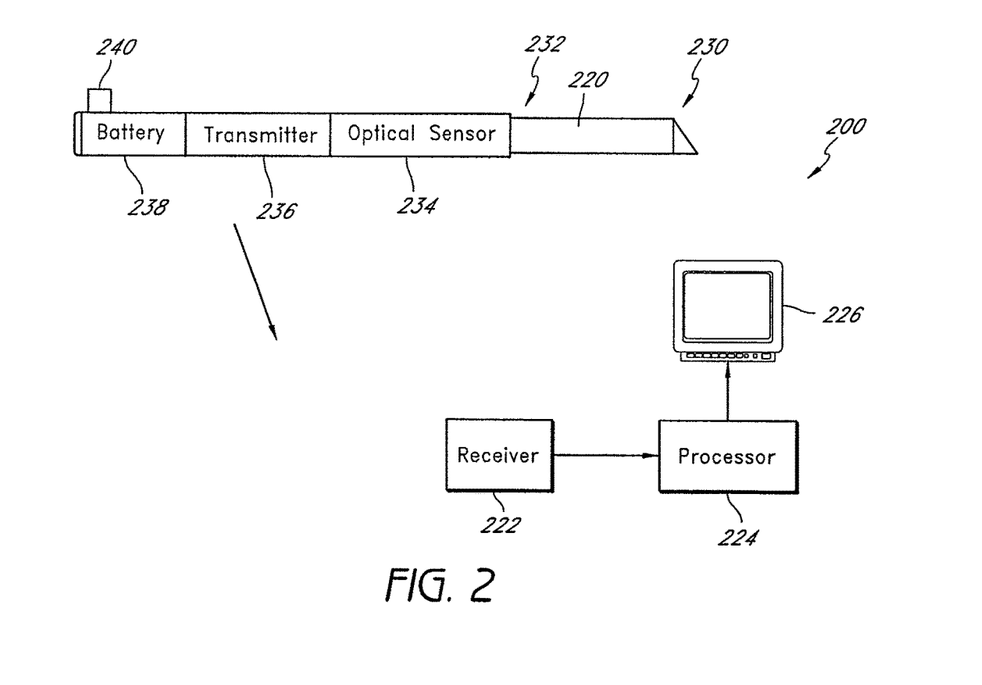
FIG. 2 illustrates another system for producing images of features inside of body parts.

FIG. 2 illustrates a system 200 that offers increased ease of use. The system 200 includes an endoscope structure 220, a receiver 222, a processor 224, and a display device 226. The endoscope shown in FIG. 2, however, is a battery operated, hand-held instrument which is configured to produce images of internal regions of a body as described above. The endoscope structure 220 shown includes a distal end 230 and a proximal end 232 and one or more solid state emitters (not shown) at the distal end that emit light to illuminate internal regions of the body. The distal end 230 of the endoscope structure 220 further includes an aperture (not shown) for collecting light emitted from the solid state emitters and reflected off of the internal regions of the body. An optical path (not shown) extends from the distal end 230 of the endoscope structure 220 to a proximal end 232.

At the proximal end 232 of the endoscope structure 220 is an optical sensor 234, a transmitter 236, a battery 238, and a control device 240. The optical sensor 234 is disposed to receive collected light and more particularly, an image of a portion of the body, and to provide an electrical signal output. At the proximal end 232, the light collected at the distal end 230 forms an image on the optical sensor 234 which produces an electrical output corresponding to the image of the illuminated internal region of the body. The electrical signal is supplied to the transmitter 236, which transmits the signal to the receiver 222. The transmitter 236 and the receiver 222 are preferably wireless. In various embodiments, the transmitter 236 comprises an RF transmitter and the receiver 222 comprises an RF receiver. The receiver 222 provides the received signal to the processor 224 that feeds signals to the display device 226. In some embodiments, the processor 224 may format the received signal so that the image of the illuminated internal region of the body can be displayed. This processor 224 may also provide additional image processing. In alternative embodiments, the optical sensor 234 provides the necessary formatting and processing and the received signal is transferred directly from the receiver 222 to the display device 226. Other distributions of functions between electronics in the optical sensor 234 and processor 224 are possible.

The battery 238 is electrically coupled to the transmitter 236, the optical sensor 234 and to the solid state emitters disposed at the distal end 230 of the endoscope structure 220. The control device 240 may be configured to allow a user of the endoscope to control the amount of current supplied by the battery 238 to the solid state emitters disposed at the distal end 230 of the endoscope structure 220. In an embodiment, the control device 240 is also configured to allow the user to selectively apply or remove a power signal from the battery 238 to the transmitter 236 and solid state emitters. This controller device 240 may comprise, for example, a rheostat or potentiometer, or digital switch, in certain embodiments. The control device may comprise a integrated circuit chip, such as a microprocessor, in certain embodiments.

The optical sensor 234, transmitter 236, and battery 238 disposed at the proximal end 232 of the endoscope structure 220 allows the endoscope structure to be a self-contained instrument that is easily maneuverable and readily mobile. The endoscope structure 220 does not need to be attached with wires or cables to provide power or to carry an image or signal to processing and display instruments. The user therefore has increased freedom to manipulate the endoscope structure and is not tethered to a console or power supply that would otherwise restrict the range of movement during a procedure. As described above, in various embodiments, the endoscope structure 220 is disposable. In an certain embodiments, the endoscope structure 220, including the solid state emitters, is disposable and is detachable from the optical sensor 234, transmitter 236, battery 238, and control device 240, which are reusable. Various design features help reduce the cost of the endoscope structure 110 and enable disposal and replacement to be a competitive alternative to reuse.

Figure 3:
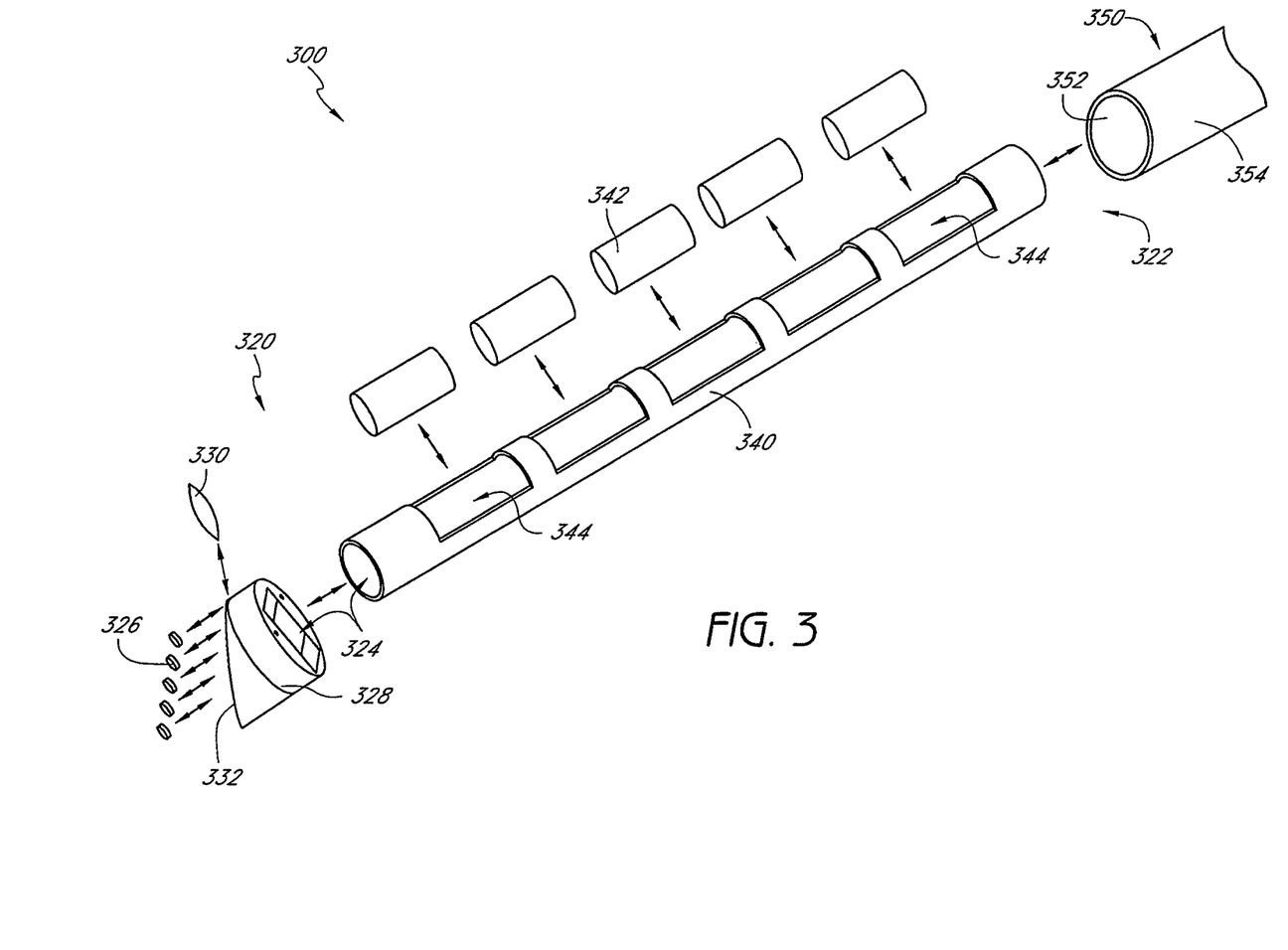
FIG. 3 is an exploded perspective view of a longitudinal member comprising an endoscope structure.

FIG. 3 illustrates an exploded perspective view of a longitudinal member 300 comprising an endoscope structure, according to various embodiments of the invention. The longitudinal member 300 has a distal end 320 and a proximal end 322. The longitudinal member 300 has a hollow inner cavity region 324 which provides an optical path from the distal end 320 to the proximal end 322.

A plurality of solid state emitters 326 (five shown) are disposed at the distal end 320 of the longitudinal member 300. In various embodiments, the solid state emitters 326 each comprise an LED. The solid state emitters are configured to emit light into the body.

At the distal end 320, the longitudinal member 300 includes a front lens holder 328 having a front surface 332 with seats to receive the solid state emitters 326. The front lens holder 328 also includes a channel therethrough that comprises a portion of the inner cavity region 324 of the longitudinal member 300. Front and rear apertures in the front lens holder 328 provide access to the channel and a path through the lens holder 328. Illumination reflected from portions of the body proceeds through this channel along this optical path. Preferably, the front lens holder 328 is configured to hold a front lens 330 that collects reflected light from the solid state emitters 326 into the inner cavity region 324 of the front lens holder 328. In certain preferred embodiments, the front surface 332 is angled so that light can be collected at the distal end 320 from an oblique direction with respect to the longitudinal member 300. For example, the longitudinal member 300 may be used to observe an inner side wall of a vessel such as a vein or artery by inserting the longitudinal member 300 longitudinally into the vessel and rotating the longitudinal member 300 such that the tilted front surface 332 is directed towards a portion of the inner side wall of the vessel desired to be imaged.

The longitudinal member 300 further includes a cradle 340 that is attachable to the front lens holder 328. The cradle 340 is configured to be a support structure for at least one optical element in the optical path from the distal end 320 of the longitudinal member 300 to the proximal end 322 of the longitudinal member 300. In various embodiments, the cradle 340 is configured to support and align multiple lens elements 342 (five shown). The lens elements 342 may comprise, for example, rod lenses. The cradle 340 is an elongated support structure comprising a hollow cylindrical tube with portions of the tube removed to form slots 344 (five shown). In various embodiments, the slots 344 are sized, configured, and positioned to receive the lens elements 342 and to align the lens elements 342 automatically along the optical path in the inner cavity region 324. Moreover, the slots 344 are preferably spaced apart to provide the appropriate spacing of the lens 342 along a longitudinal direction and optical axis as defined by the lens prescription.

The longitudinal member 300 further comprises an outer tube 350. The outer tube 350 includes an inner region 352 and an outer region 354. With the lens elements 342 disposed in the slots 344 of the cradle 340, the cradle 340 can be slid into the inner region 352 of the outer tube 350. The outer tube 350 may shield and protect the cradle 340 and lens elements 342.

In certain embodiments, the outer region 354 of the outer tube 350 comprises a heat conducting material such as aluminum, stainless steel, or the like. In such an embodiment, the outer tube 350 may conduct heat generated by the solid state emitters 326 away from the distal end 320 of the longitudinal member 300. In other embodiments, other portions of the outer tube 350, the cradle 340, and/or lens holder 328 may comprise thermally conducting material. Conductive material may be deposited on the outer tube 350, the cradle 340 and/or the lens holder 328 in certain embodiments. For example, these components may comprise ceramic or plastic with portions having metallization formed thereon by, for example, electroplating or electrochemically deposition. In certain embodiments, the outer tube 350 comprises stainless steel and a portion of this outer tube 350 is electroplated with aluminum for heat conduction and/or electrical connection. Other designs are possible.

Although not shown, a diffuser or a plurality of diffusers may be disposed in front of the solid state emitters 326. The diffuser or plurality of diffusers are configured to disperse the light from the solid state emitters 326.

In operation, at least the distal end 320 of the longitudinal member 300 is inserted into a body cavity. An electrical power signal is provided to the solid state emitters 326 by thin electrical wires (not shown) or electrical traces (not shown) that may be disposed along a surface of the cradle 340 and front lens holder 328. The electrical power signal causes the solid state emitters 326 to emit light having an intensity proportional to the electrical power signal. In the case where the longitudinal member 300 comprise conducting material such as metal, the conducting longitudinal member 300 may operated as an electrical path for providing power or grounding to the emitters 326.

The light is reflected off an object within the body cavity or the inner walls of the body cavity. A portion of the reflected light is collected into the inner cavity region 324 of the front lens holder 328 through an aperture (not shown) in the front surface 332. As discussed above, the light may be collected by a front lens 330. The light is then directed through the plurality of lens elements 342 disposed in the cradle 340. Thus, the light propagates from the distal end 320 of the longitudinal member 300 to the proximal end 322 of the longitudinal member 300. The lens elements 342 are preferably positioned and aligned by the cradle so as to relay an image of the illuminated object or inner wall.

The solid state emitters 326 generate heat as they emit light. The heat is preferably conducted away from the distal end 320 of the longitudinal member 300 by the heat conducting surface 354 of the outer tube 350. In other embodiments, other portions of the outer tube, the cradle 340 and/or lens holder 328 may comprise thermally conductive material or layers so as to transfer heat produced by the emitters 326. Increased thermal conduction permit the emitters 326 to be driven with more power so as to emit more light. In some embodiments, the LEDs are driven with a current of up to 40 or 60 milliamps or more.

Preferably, the longitudinal member 300 has a small cross-section for example less than 3 or 4 millimeters across in some embodiments. The small size of the emitters facilitates such small cross-sections. As described above, the small cross-section reduces trauma and damage to the body in which the endoscope is inserted.

In various embodiments, the longitudinal member 300 is disposable. The lenses 342 may comprise compression molded glass, which can be manufactured relatively inexpensively such that the longitudinal member 340 together with the emitters 326 and the lens may be disposed of after a single use and remain cost-effective in comparison with conventional endoscope designs. In certain embodiments, the longitudinal member is sterilizable.

Figure 4:
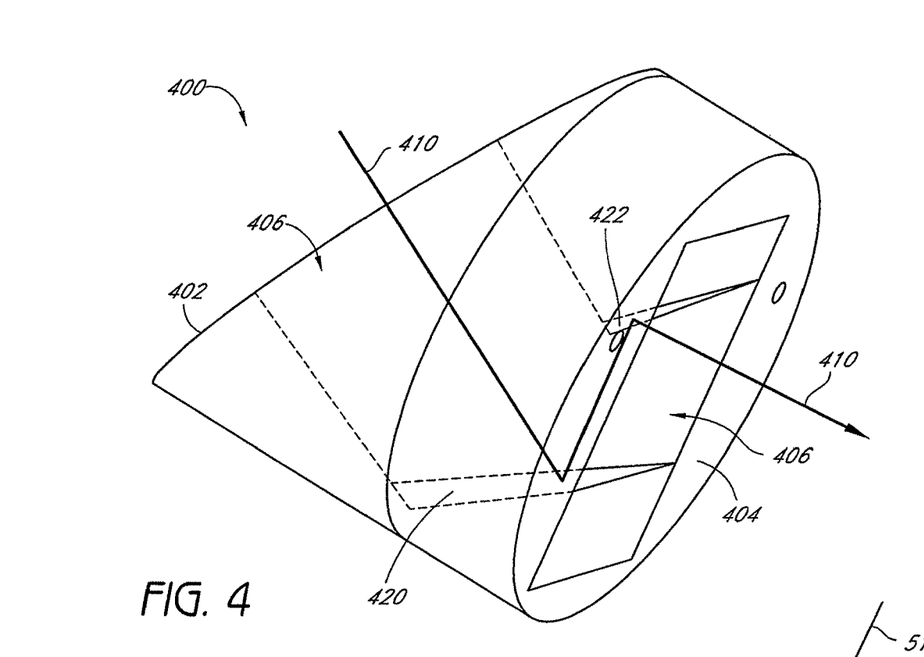
FIG. 4 is a rear perspective view of an exemplary front lens holder that may be used with the longitudinal member of FIG. 3.

FIG. 4 is a rear perspective view of an exemplary front lens holder 400 for use with a longitudinal member of an endoscope, such as the longitudinal member 300 shown in FIG. 3. The front lens holder 400 comprises a front surface 402, a rear surface 404, and an inner cavity region 406. The front surface 402 and the rear surface 404 each comprise an aperture to the inner cavity region 406. For illustrative purposes, FIG. 4 shows an optical path 410 entering the aperture on the front surface 402, passing through the inner cavity region 406 and out the aperture of the rear surface 404.

The front surface 402 is tilted with respect to the rear surface 404 of the front lens holder 400. The tilted front surface 402 allows the front lens holder 400 to collect light reflected from of objects located to the side of an endoscope. In exemplary embodiments, the front surface 402 is tilted between about 30° and 70° with respect to the rear surface 404. In certain embodiments, for example, this tilt may be about 45°. However, it should be noted that the tilt of the front surface 402 can be selected to provide the user of the endoscope with the ability to view objects located to the side of the endoscope according to any number of angle ranges, including but not limited to a flat surface parallel to the rear surface 404. In some of these embodiments, solid state emitters (not shown) located on the front surface 402 may be angled, for example, so as to emit light at an angle to illuminate objects to the side of the endoscope. The lens (not shown) in the lens holder 400 may also be tilted to collect light reflected or scattered from the sidewalls of the body cavity.

The front lens holder 400 is configured to redirect the light entering the front lens holder 400 through the aperture in the front surface 402 to exit the front lens holder 400 through the aperture in the rear surface 404 so as to convey an image of an object along an optical path through the endoscope. In certain embodiments, the light entering the front lens holder 400 is redirected using an optical element such as a prism (not shown) comprising one or more reflective surfaces. In various preferred embodiments, however, the light entering the front lens holder 400 is redirected using a first reflective surface 420 and a second reflective surface 422. Preferably, the first and second reflective surfaces 420, 422 do not comprise glass. These reflective surfaces 420, 422 may comprise a reflective layer such as metallization formed on a surface of the lens holder 400.

FIG. 4 illustrates the first reflective surface 420 and the second reflective surface 422 walls defining the inner cavity region 406. The first reflective surface 420 and the second reflective surface 422 are angled such that the optical path 410 of the light entering the cavity region 406 approximately perpendicular to the front surface 402 will be redirected so as to exit the cavity region 406 approximately perpendicular to the rear surface 404. Thus, for example, light entering the longitudinal member 300 shown in FIG. 3 will be redirected and conveyed through the inner cavity region 324 from the distal end 320 to the proximal end 322 through the plurality of rod lenses 342.

Figure 5:
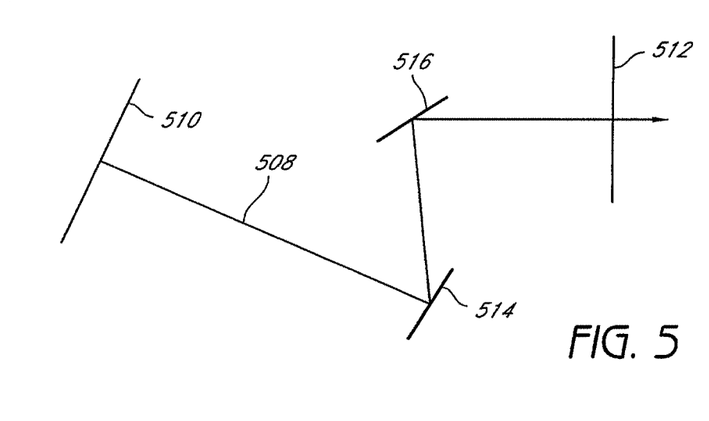
FIG. 5 shows a schematic diagram of an optical path through a front surface tilted at an angle with respect to a rear surface.

To illustrate the concept of redirecting light through the front lens holder 400, FIG. 5 shows a schematic diagram of an optical path 508 through a front surface 510 tilted at an angle with respect to a rear surface 512. The optical path 508 passes approximately perpendicular through the front surface 510 and intersects with a first reflective surface 514 positioned and angled so as to redirect the optical path 508 to a second reflective surface 516. The second reflective surface 516 is positioned and angled so as to redirect the optical path 508 approximately perpendicularly through the rear surface 512. In other embodiments, the front surface 510 and rear surface 512 may not be perpendicular to this optical path 508, however, preferably the first and second reflective surfaces 514, 516 are oriented to direct the optical path through the length of the elongated member.

Referring again to FIG. 4, the first and second reflective surfaces 420, 422 are substantially specularly reflective. The first and second reflective surfaces 420, 422 may, for example, be smooth, planar surfaces. The front lens holder 400 may be formed from materials that can be molded or machined. In various embodiments, the front lens holder 400 is formed of a material selected from the group comprising plastic, ceramic, or metal such as nickel or the like. In certain preferred embodiments, the first and second reflective surfaces 420, 422 are polished until they are substantially smooth. For example, the first and second reflective surfaces 420, 422 may be polished down to average roughness of approximately eight Angstroms. After polishing, the first and second surfaces may be metallized with a substantially reflective material, such as nickel, chrome or the like. Other reflective layers may be employed as well. In certain embodiments, the substantially reflective material is electroplated or electrochemically deposited onto the polished surfaces. For example, in various exemplary embodiments, the lens holder comprises molded or machined plastic or ceramic that is electroplated to form reflective metal layers. Nickel electroforming, for example, may be employed to create the first and/or second reflective surfaces 420, 422. Such processes are well-developed and relatively inexpensive and can be readily implemented in manufacturing processes.

Forming reflective surfaces on the inner walls of the lens holder offers several advantages. Integrating the reflective surfaces into the lens holder reduces the number of elements that need to be optically aligned. For example, once the reflective surfaces have been formed on the interior walls of the lens holder, precise alignment may be achieved by simply inserting or "snapping" the lens holder 400 in place on the longitudinal member 300. In contrast, microscopes are employed to align tiny prisms in conventional designs. These micro-prisms are also substantially more expensive. For example, injection molding the lens holder 400, polishing inner surfaces on the lens holder, and performing Ni electroforming or chrome electroplating may be relatively less expensive in comparison to polishing tiny glass microprisms. The reduced cost yielded by such designs may permit the endoscope to be disposable.

Figure 6:
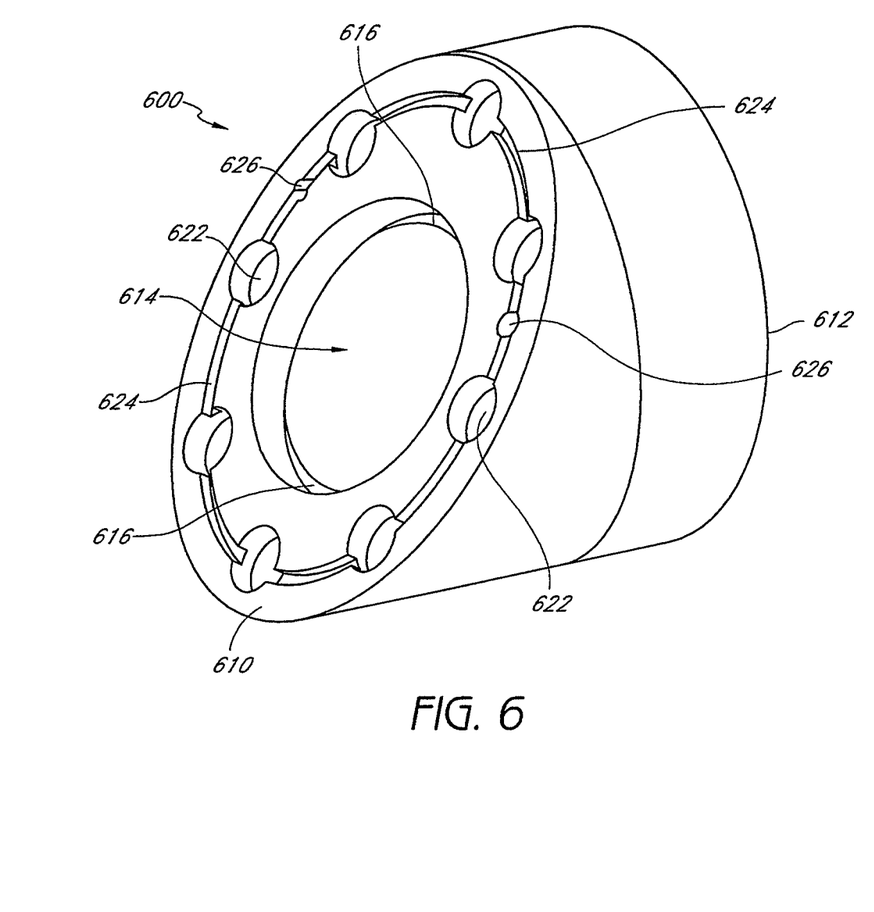
FIG. 6 shows another view of a front lens holder for used with a longitudinal member, such as the longitudinal member of FIG. 3.

FIG. 6 provides another view of a front lens holder 600 for use with a longitudinal member of an endoscope, such as the longitudinal member 300 shown in FIG. 3. FIG. 6 is a partial front perspective view of the front lens holder 600. The front lens holder 600 comprises a front surface 610 and a rear surface 612. A hollow interior region 614 extends from an aperture in the front surface 610 to an aperture in the rear surface 612. In various embodiments, the front lens holder 600 includes a lens seat 616 configured to hold a lens (not shown) which covers the aperture in the front surface 610. The specifications of the lens, e.g., power, numerical aperture, etc., are preferably selected to direct light into the front lens holder 600. Alternatively, the aperture in the front surface 610 may be covered with a window or material (not shown) that is transparent to selected wavelengths of light. A lens may be disposed in the inner region 614 of the lens holder 600 or may be exterior to the lens holder in some embodiments. The hollow interior region 614 may be hermetically sealed and may be filled with a gas or liquid. Alternatively, the hollow interior region 614 may be a vacuum.

The front surface 610 of the front lens holder 600 includes a plurality of seats 622 (eight shown) configured to hold solid state emitters (not shown), such as LEDs. The seats 622 are positioned around the aperture in the front surface 610. The seats 622 are positioned such that light emitted from their respective locations will be reflected from an object back through the aperture in the front surface 610. In various embodiments, the seats are arranged to provide substantially uniform illumination.

The front surface 610 also includes a path 624 for electrical power. In an embodiment, the path 624 is shaped to hold thin electrical wires connecting the solid state emitters to an electrical power source. Alternatively, the path 624 comprises a conductive trace for providing power to the solid state emitters. The path 624 may be connected to one or more through-holes 626 (two shown) to electrically couple power from a power source (not shown).

As described above, the front lens holder 600 may be formed, for example, by molding, machining, or other manufacturing processes. The lens holder may comprise two or more separable pieces that are fit together. Such designs may facilitate manufacture such as polishing the inner surfaces to form reflective portions of the interior sidewalls. In various embodiments, the front lens holder 600 is disposable and/or sterilizable.

Figures 7, 8:
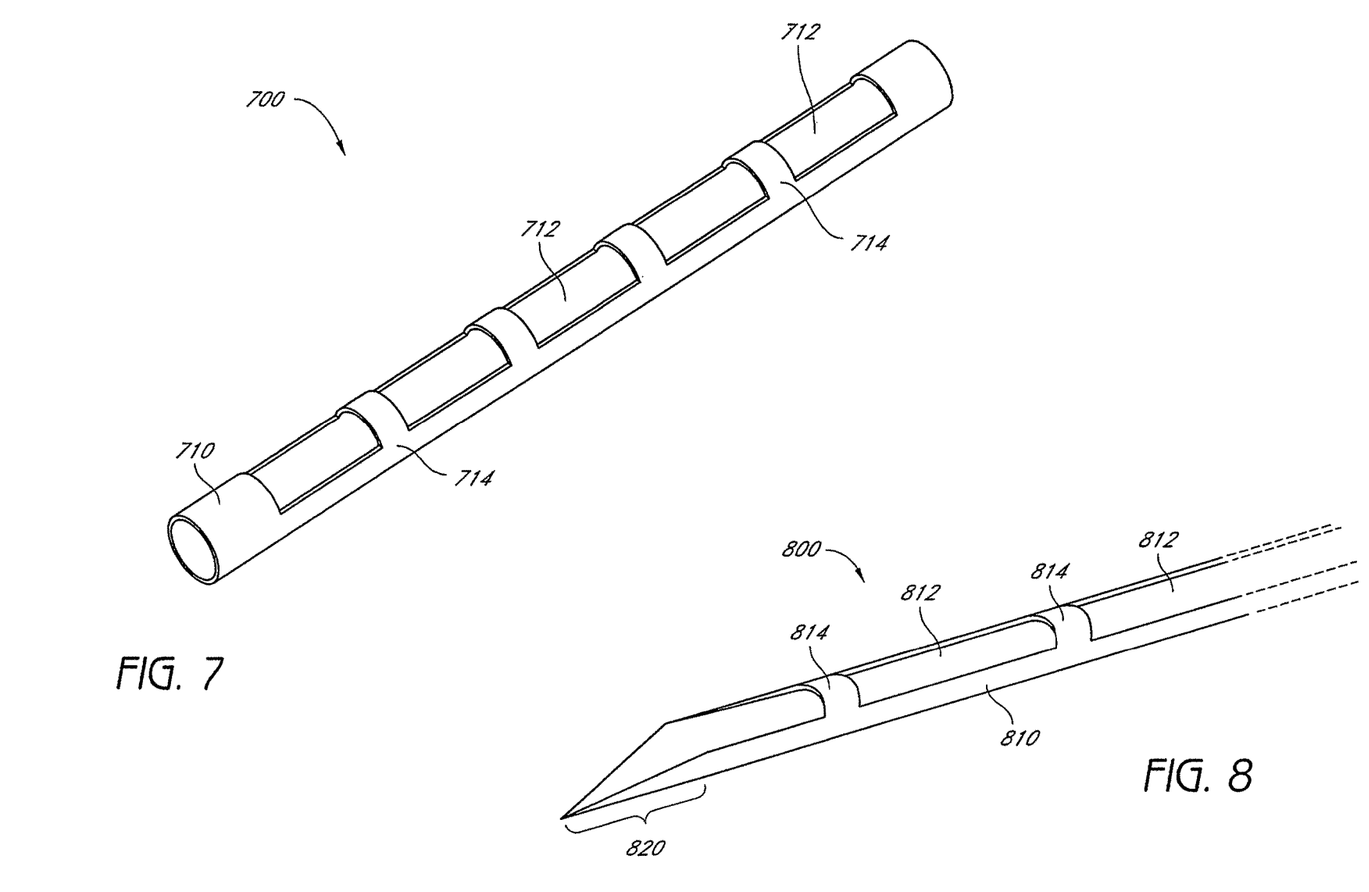
FIG. 7 is a perspective view of an elongated support structure, which may be used as the cradle of FIG. 3.
FIG. 8 is a partial perspective view of an exemplary slotted elongate support structure, which may also be used as the cradle of FIG. 3.

FIG. 7 is a perspective view of an elongated support structure 700, which can be used as a cradle, such as the cradle 340 shown in FIG. 3. The elongated support structure 700 comprises a hollow tube 710 having a plurality of slots 712 (five shown) each configured to hold a lens such as a rod lens (not shown) or other optical element. The slots 712 are separated by spacer portions 714 (four shown) that are each sized and positioned so as to provide proper alignment and longitudinal separation of the rod elements for suitable relay of an image therethrough. In other words, the spacing between the slots 712 are defined by the spacer portions 714 so as to longitudinally space the rod lenses with respect to each other according to the optical design prescription.

The elongated support structure 700 may be formed, for example, by molding, machining, or other manufacturing processes. The elongated support structure 700 may comprise, for example, plastic, ceramic, or metal. In certain embodiments, one or more electrical traces or paths may be formed on a surface of the elongated support structure 700 to provide electrical power to solid state light emitters (not shown). In various embodiments, the elongated support structure 700 is sterilizable and/or disposable.

FIG. 8 is a partial perspective view of another exemplary slotted elongate support structure 800 which can be used as a cradle, such as the cradle 340 shown in FIG. 3. The slotted elongate support structure comprises a hollow tube 810 having slots 812 configured to hold lens such as rod lens (not shown) or other optical elements. The slots 812 are separated by spacing elements 814 (two shown) that are each sized and positioned so as to provide proper longitudinal separation of the rod elements for suitable propagation of an image. The slots 812 are preferably positioned to provide proper lateral positioning of the lens or other optical elements as well.

The slotted elongate support structure 800 also includes a tapered "V" shaped portion 820 that is pointed at one end. The tapered "V" shaped portion 820 is configured to facilitate the insertion of the slotted elongate support structure 800 into an outer tube, such as the outer tube 350 shown in FIG. 3. When aligning the slotted elongate support structure 800 with an outer tube, the point of the "V" shaped member 820 is preferably sufficiently small so as to be easily inserted into the outer tube. The "V" shaped member 820 also simplifies the manufacturing process by properly aligning the slotted elongate support structure 800 with an outer tube upon insertion therein.

The slotted elongate support structure 800 may have other shapes as well. In certain embodiments, for example, the slotted elongated support structure may be "V" shaped having a "V" shaped lateral cross-section over a substantial portion of its length.

The features described herein can be employed alone or in various combinations to create improved endoscopes designs. For example, endoscope structures having solid state emitters may be employed together with a lens holder that does not include a prism. Alternatively, the lens holder designs described herein can be employed with conventional illumination approaches such as use of a fiber optic bundle instead of LEDs. Similarly, the slotted elongated support structure may be employed with or without solid state emitters and with or without the lens holder having reflective interior sidewalls for directing an image through an array of lenses. A wide range of designs are possible.

Also, although FIG. 3 depicts rod lenses being disposed in the endoscope structure, in various embodiments, other types of lenses such as lenses having reduced longitudinal thickness may be employed. Rod lenses advantageously increase optical throughput by increasing the Lagrange invariant. However, a plurality of small bright solid state light emitters, such as LED's, may provide substantially illumination. The solid state emitters, together with their electrical power connections, however, do not occupy as much area across a lateral cross-section of the endoscope structure as a fiber optic bundle used for illumination in conventional endoscope designs. Accordingly, room is available for larger diameter lenses having higher numerical aperture and throughput when using tiny solid stated emitters. With increased throughput, lenses thinner than rod lens may be employed. The reduced Lagrange invariant is offset by the increase in diameter of the lenses. The throughput may be larger in some cases where thin lenses are employed instead of rod lenses. Likewise, rod lenses may or may not be employed in combination, for example, with the lens holder having internal reflecting sidewalls and/or the slotted elongate support structure. For example, in certain embodiments, the elongate support structure may have slots with reduced length to accommodate lenses other than rod lenses. In general, rod lenses are more expensive than thin lenses. Accordingly, the manufacturing cost of the endoscope can be reduced.

As described above, various combination and arrangements may be employed. Accordingly, the structures and apparatus should not be limited to those particular designs shown in FIGS. 1-8 or specifically disclosed in the description of these figures. Other embodiments are possible as well. These embodiments may include features well known in the art as well as feature not yet devised.

As described above, the process of manufacturing the endoscope devices may be simplified or improved. In certain embodiments, for instance, the lenses can be automatically positioned in the cradle so as to have suitable spacing between lenses to relay an image in the body. Such a method of forming an endoscope apparatus having proximal and distal ends may comprise, for example, providing an elongated support structure having a plurality of sites for insertion of optical elements and inserting a plurality of lenses at the sites. The elongated support structure may be inserted into a hollow outer protective shield having an open inner region. Preferably, the plurality of sites are laterally positioned and longitudinally spaced with respect to each other so as to provide an aligned optical system that relays an image from the distal end portion to the proximal end portion. Such manufacture may be implemented partially or totally robotically in certain cases. Such automated processes may reduce the cost of manufacture.

In other various embodiments, a front endpiece may be attached at the distal end portion of an endoscope assembly. The front endpiece preferably has an open inner region for receiving light to form images of portions of a body. A plurality of solid state light emitters are preferably affixed to the front endpiece to illuminate the body portions. A lens is mounted to the front endpiece to receive light from the body portions. At least one reflective surface is formed on a sidewall of the inner open region of the front endpiece to reflect light received from the body portions through the plurality of lenses.

Other manufacturing methods may include molding the front endpiece so as to include the sidewall surface on the inner open region for forming the reflective surface with a shape and orientation to produce the image. The reflective surface may be formed by metalizing the sidewall surface. In certain embodiments, the sidewall surface is polished prior to metallization.

In other embodiments, a method for manufacturing a front end of an endoscope for viewing portions of a body comprises forming a front endpiece for receiving light from the body portions so as to enable viewing of the body portions. An inner cavity region is formed in the front endpiece to allow passage of the light from the body portions and at least one substantially planar sidewall surface is formed in the inner cavity region. The method also includes metalizing the at least one substantially planar sidewall surface so as to form a substantially reflective surface that reflects the light received from the body portions. The sidewall surface may be polished prior to metallization to create a substantially smooth surface.

At least one seat is preferably formed in the front endpiece for placement of one or more solid state light emitters to illuminate the body portions. A lens seat may be formed in the front endpiece for mounting a lens to receive light from the body portions. In certain embodiments, the front endpiece is formed by molding. In some embodiments, at least a portion of the front endpiece is formed by machining.

Various combinations of manufacturing steps may be employed with more or less steps and the specific method should not be limited to the specific processes recited herein. A wide range of fabrication methods are possible.

While the present invention has been disclosed in detail and by way of exemplary embodiments, those of ordinary skill in the art will recognize and appreciate that the invention is not so limited. Those of ordinary skill in the art will recognize and appreciate that many additions, deletions and modifications to the disclosed embodiment and its variations may be implemented without departing from the scope of the invention, which is limited only by the appended claims and their legal equivalents.

What is claimed is:

1. An endoscope having proximal and distal end portions for viewing features inside a cavity of a body into which said distal end portion of said endoscope is inserted, said endoscope comprising:
   a longitudinal member comprising:
   an elongated support structure and an outer tube extending from said distal end portion to said proximal end portion, said longitudinal member having an inner cavity region and said outer tube having an inner region, said elongated support structure disposed in said inner region of said outer tube;
   an optical path through said inner cavity region of said longitudinal member for propagating light from said distal end portion to said proximal end portion of said endoscope;
   a front member proximate to said distal end portion and disposed such that the optical path extends through the front member, said front member having a distally facing tilted front surface having a distally facing tilted aperture therein to receive light from said cavity of the body said front member comprising:
   a first specularly reflective surface disposed along said optical path at said distal end portion of said longitudinal member, said first specularly reflective surface angled such that light can be collected through said distally facing tilted aperture in said distally facing tilted front surface at said distal end portion from an oblique direction with respect to said longitudinal member;
   a second specularly reflective surface disposed along said optical path at said distal end portion of said longitudinal member, said second surface oriented to receive light from said first specularly reflective surface and reflect said light longitudinally through said inner cavity region of said longitudinal member, wherein the first and the second specularly reflective surfaces are not movable with respect to inner sidewalls of the front member; and
   one or more solid state emitters having an electrical input and an optical output, said one or more emitters radiating light when activated so as to illuminate at least a portion of said cavity of a body,
   a plurality of lenses disposed along said optical path extending from the second specularly reflective surface to said proximal end portion, the plurality of lenses configured to convey light along said optical path, said elongated support structure supporting said plurality of lenses in said optical path;
   an electrically conducting path from said proximal end portion to said distal end portion, said electrically conducting path configured to provide electrical power to said one or more solid state emitters at said distal end portion; and
   an optical sensor disposed at said proximal end portion, said optical sensor comprising an electrical power input and electrical signal output;
   wherein said optical path does not include an optical element disposed between the first specularly reflective surface and the second specularly reflective surface,
   wherein the optical path does not include an optical element disposed between the second specularly reflective surface and the plurality of lenses, and
   wherein the elongate support structure comprises thermally conducting material to conduct heat generated by the one or more, solid state emitters.

2. The endoscope of claim 1, wherein said front member is monolithic and said first specularly reflective surface and the second specularly reflective surface are disposed on said monolithic front member.

3. The endoscope of claim 1, wherein said first and second specularly reflective surfaces comprise ceramic, plastic or metal.

4. The endoscope of claim 1, wherein said one or more solid state emitters are arranged around said distally facing tilted aperture at said distal end portion of said longitudinal member.

5. The endoscope of claim 1, wherein said one or more solid state emitters are at said distal end portion of said longitudinal member.

6. The endoscope of claim 1, further comprising a lens element in said distal end portion of said longitudinal member for collecting light emitted from said one or more solid state emitters and reflected from features in said cavity of said body.

7. The endoscope of claim 1, wherein said one or more solid state emitters comprise one or more light emitting diodes.

8. The endoscope of claim 1, wherein said optical sensor comprises a detector array disposed with respect to said proximal end portion to receive an image propagated along said optical path from said distal end portion.

9. The endoscope of claim 1, wherein the first specularly reflective surface comprises a planar metal surface.

10. The endoscope of claim 9, wherein the second specularly reflective surface comprises a planar metal surface.

11. The endoscope of claim 10, wherein said first and second specularly reflective surfaces comprise ceramic, plastic or metal.

12. The endoscope of claim 1, wherein the first specularly reflective surface is disposed along a planar surface of the longitudinal member.

13. The endoscope of claim 12, wherein the second specularly reflective surface is disposed along a planar surface of the longitudinal member.

14. The endoscope of claim 13, wherein said first and second specularly reflective surfaces comprise ceramic, plastic or metal.

15. The endoscope of claim 1, wherein said first specularly reflective surface comprises a first metalized surface and said second specularly reflective surface comprises a second metalized surface.

16. The endoscope of claim 1, wherein the longitudinal member comprises a proximal end and the front member comprises a distal end, and wherein the endoscope extends linearly in a straight direction from the proximal end of the longitudinal member to the distal end of the front member.

17. The endoscope of claim 1, wherein said plurality of lenses comprise one or more compression molded lenses.

18. The endoscope of claim 1, wherein said optical path includes air between the first specularly reflective surface and the second specularly reflective surface.

19. The endoscope of claim 1, wherein light collected at the distal end portion is reflected at an interface of the first reflective surface and air.

20. The endoscope of claim 1, wherein light received from the first reflective surface is reflected at an interface of the second specularly reflective surface and air.

21. The endoscope of claim 1, wherein said endoscope support structure is configured to provide said electrically conducting path.

22. The endoscope of claim 21, further comprising one or more electrical traces or paths formed on a surface of the elongated support structure to provide electrical power to said one or more solid state emitters.

23. The endoscope of claim 1, wherein said outer tube comprises thermally conducting material.

24. The endoscope of claim 1, wherein the elongated support structure comprises conducting material configured to be operated as said electrically conducting path for providing power to said one or more solid state emitters.

25. The endoscope of claim 1, wherein a width of a cross-section of the longitudinal member is less than 4 millimeters.

* * * * *

UNITED STATES PATENT AND TRADEMARK OFFICE
CERTIFICATE OF CORRECTION

PATENT NO. : 10,448,806 B2
APPLICATION NO. : 13/786220
DATED : October 22, 2019
INVENTOR(S) : George Wright et al.

Page 1 of 1

It is certified that error appears in the above-identified patent and that said Letters Patent is hereby corrected as shown below:

In the Claims

In Column 14, Line 51, Claim 1, delete "more," and insert -- more --.

Signed and Sealed this
Twenty-eighth Day of April, 2020

Andrei Iancu
*Director of the United States Patent and Trademark Office*